United States Patent [19]

Murase et al.

[11] 3,996,790

[45] Dec. 14, 1976

[54] APPARATUS FOR MEASURING SATURATION TEMPERATURE OF LIQUID METAL OXIDE

[75] Inventors: Michio Murase, Kawasaki; Isao Sumida; Koichi Kotani, both of Sagamihara, all of Japan

[73] Assignee: Hitachi, Ltd., Japan

[22] Filed: July 17, 1974

[21] Appl. No.: 489,120

[30] Foreign Application Priority Data

July 17, 1973   Japan .............................. 48-79875

[52] U.S. Cl. ............................... 73/61 LM; 73/15 R
[51] Int. Cl.² ......................................... G01N 11/00
[58] Field of Search ........................ 73/61 LM, 15 R

[56] References Cited
UNITED STATES PATENTS

| | | | |
|---|---|---|---|
| 2,782,369 | 2/1957 | Werner et al. | 73/61 LM UX |
| 2,997,874 | 8/1961 | Billuris et al. | 73/61 LM |
| 3,343,401 | 9/1967 | Delisle | 73/61 LM X |
| 3,462,997 | 8/1969 | Roach et al. | 73/61 LM |
| 3,672,209 | 6/1972 | Roach et al. | 73/61 LM |

*Primary Examiner*—Richard C. Queisser
*Assistant Examiner*—Joseph W. Roskos
*Attorney, Agent, or Firm*—Craig & Antonelli

[57] ABSTRACT

In this invention, the liquid metal passage is branched into a high temperature passage and a low temperature passage cooled by cooling means, and in a coupling passage connecting these high temperature and low temperature passages, high temperature liquid metal and low temperature liquid metal are flown in the state facing each other and they are thus mixed in this coupling passage. In this manner, the flow variation owing to deposition of the oxide in the cooled passage is detected, and the saturation temperature of an oxide is determined from the temperature at which the flow variation occurs.

9 Claims, 6 Drawing Figures

APPARATUS FOR MEASURING SATURATION TEMPERATURE OF LIQUID METAL OXIDE

BACKGROUND OF THE INVENTION

This invention relates to an apparatus for measuring the saturation temperature of an oxide in liquid metal. More particularly, the invention relates to an apparatus for measuring the saturation temperature of an oxide in liquid metal in various devices using liquid metals, such as a fast breeder reactor, a chemical plant or the like.

Measurement of the saturation temperature of an oxide in liquid metal has heretofore been performed by a method in which flow variation owing to deposition of an oxide is determined by electromagnetic means, a method in which an oxide is deposited on a flow passage to plug the passage with the oxide and the saturation temperature of the oxide is determined with respect to the deposited oxide. These conventional methods, however, are defective in that the structure of the measurement apparatus is complex or since it takes a long time to restore the ordinary operation state from the plugged state, continuous measurement is impossible.

SUMMARY OF THE INVENTION

It is a primary object of this invention to provide an apparatus by which the saturation temperature of an oxide in liquid metal can be measured relatively easily and relatively effectively.

Another object of this invention is to provide an apparatus by which the saturation temperature of an oxide in liquid metal can be continuously measured.

In order to attain the foregoing objects, in this invention the flow passage of liquid metal is divided into two branch passages (or branch tubes) and one of them is cooled, and high temperature liquid metal and low temperature liquid metal in both the passages are flown into a coupling passage (or a coupling tube) in the state facing each other and thus both the liquids are mingled in this coupling passage. Thus, the flow variation owing to deposition of an oxide in the cooled passage is detected by measuring the temperature in the coupling passage, or is directly detected by means of a flow meter, and the saturation temperature of the oxide is determined from the temperature at which the flow variation occurs.

As is apparent from the foregoing, in this invention the saturation temperature of the oxide in liquid metal is determined based on the flow variation in the liquid metal in the low temperature passage. Therefore, plugging of the low temperature passage such as conducted in conventional methods need not be effected in this invention. If the low temperature passage be plugged in the apparatus of this invention, plugged deposits will be cleared only by projecting to the plugged deposits high temperature liquid metal in the high temperature passage.

DESCRIPTION OF THE PREFERRED EMBODIMENTS

Figure 1:
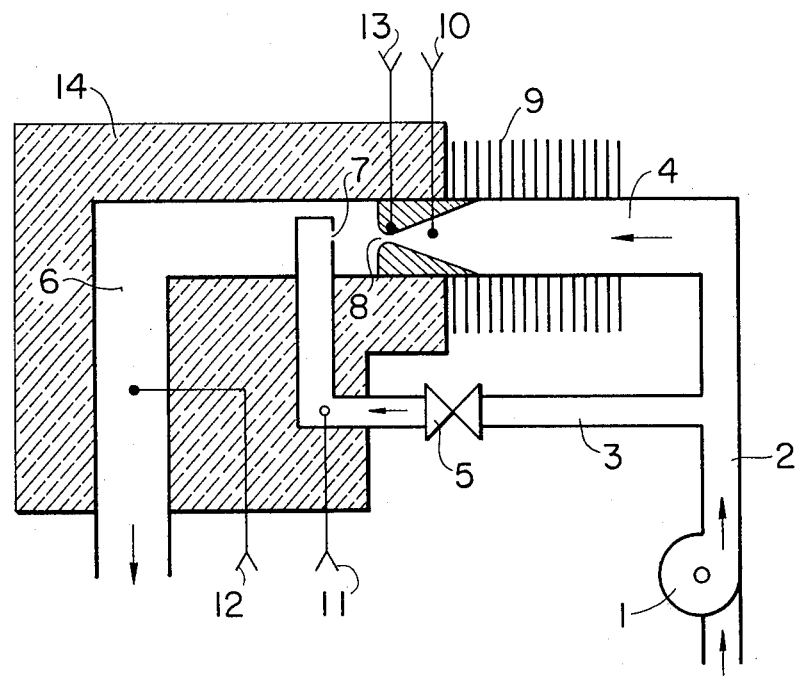
FIG. 1 is a diagram illustrating the section of an embodiment of the apparatus of this invention.

The principle of this invention will now be described.

From the thermal energy preservation equation, the following two equations can be derived:

$$(Th - Te)Qe = (Th - Tt)Qt \qquad (1)$$

$$Qe = \frac{(Th - Tt)}{(Th - Te)} \times Qt = \alpha \cdot Qt \qquad (2)$$

wherein:
- $Te$: temperature of liquid metal in low temperature passage
- $Th$: Temperature of liquid metal in high temperature passage
- $Tt$: temperature of liquid metal in coupling passage
- $Qe$: flow amount of liquid metal in low temperature passage
- $Qt$: flow amount of liquid metal in coupling passage
- $\alpha$: ratio of flow amount in low temperature passage to flow amount in coupling passage at the time of deposition of oxide.

In case the oxide is deposited in the low temperature passage, if $Qeo$ is used for $Qe$ at the time when no oxide is deposited in the low temperature passage and supposed that the back pressure in the passage is kept constant, the flow amount $Qe$ is expressed as follows by using the equation (2):

$$Qe = \frac{R^2}{Ro^2} \cdot Qeo = \frac{R^2}{Ro^2} \cdot \alpha_o \cdot Qt = \alpha \cdot Qt \qquad (3)$$

wherein:
- $Ro$: outlet diameter of low temperature passage at the time when no oxide is deposited
- $R$: outlet diameter of low temperature passage at the time of deposition of oxide
- $\alpha_o$: ratio of flow amount in low temperature passage to flow amount in coupling passage at the time when no oxide is deposited Accordingly, the flow ratio $\alpha$ is expressed by the following equation $$\alpha = \frac{R^2}{Ro^2} \cdot \alpha_o \qquad (4)$$

and hence, it is seen that the flow ratio $\alpha$ changes in proportion with the square of the diameter of the low temperature passage tube. Therefore, deposition of an oxide in the low temperature passage can be detected depending on the change of the flow ratio $\alpha$.

As is apparent from the equation (2), the flow ratio $\alpha$ is expressed by the following formula $$\alpha = \frac{Th - Tt}{Th - Te} \qquad (5)$$

Therefore, the flow ratio α is determined from the measured values of Th, Te and Tt.

In the apparatus of this invention, the saturation temperature of an oxide in liquid metal is measured according to the foregoing principle. Accordingly, the apparatus of this invention comprises two branch passages, a coupling passage connecting said two branch passages, outlets for projecting high temperature liquid metal and low temperature liquid metal in said two branch passages into the coupling passage in the state facing each other to thereby mix said two liquid metals in the coupling passage, a cooler for cooling one of the branch passages, and devices for measuring the temperature of high temperature liquid metal, the temperature of low temperature liquid metal, the temperature of the liquid metal mixture and the temperature of the liquid metal-projecting outlet disposed on the side of the low temperature passage, respectively.

The following advantages can be attained by the apparatus of this invention for measuring the saturation temperature of an oxide in liquid metal, which has the above structure:

1. The flow variation owing to deposition of the oxide can easily be detected only by measuring temperatures.
2. The flow ratio α is not influenced by the change of the flow amount in the main passage caused by power variation in a driving pump or other factor. Therefore, the flow ratio α can be determined with high precision only by measuring temperatures.
3. The degree of deposition of the oxide can be known directly from the variation of the flow ratio α.
4. The deposited oxide can easily be molten by projecting high temperature liquid metal of the high temperature passage to the deposited oxide. Therefore, flow conditions can be automatically recovered.

This invention will now be described by reference to the accompanying drawings.

By referring to FIG. 1 showing the section of an embodiment of the apparatus of this invention, a main passage 2 coming from a pump 1 is divided into a high temperature passage 3 and a low temperature passage 4. A valve 5 is mounted on the high temperature passage to distribute the liquid metal flow into the passages 3 and 4. Liquid metal flows in the high temperature and low temperature passages 3 and 4 pass through an orifice 7 and a nozzle 8, respectively, and are joined in a coupling passage 6 heat-insulated by an adiabatic material 14. The nozzle 8 and orifice 7 are disposed to face each other. Any of nozzles and orifices can be used as the members 7 and 8. Thermocouples 11, 10 and 12 are used for measuring the temperature of the high temperature passage 3, the temperature of the low temperature passage 4 and the temperature inside the coupling passage 6, respectively.

The operation of the apparatus of this invention having the above structure is conducted in the following manner:

The pump 1 and a cooler 9 are actuated to project low temperature liquid metal from the low temperature passage 4 through the nozzle 8. When high temperature liquid metal is projected from the high temperature passage 3 through the orifice 7 by operating the valve 5, the high temperature liquid metal is mixed with the low temperature liquid metal in the coupling passage 6, and the mixed liquid metal flow is discharged from the coupling passage.

The liquid temperature Te in the low temperature passage 4 is reduced by cooling and the flow ratio α is measured. The valve 5 mounted on the high temperature passage 3 is adjusted so as to obtain an appropriate flow ratio α.

When the liquid temperature in the low temperature passage 4 is reduced below the saturation temperature of the oxide, the oxide is deposited in the periphery of the nozzle 8 to thereby reduce the sectional area of the nozzle 8. Therefore, the flow amount in the low temperature passage 4 decreases and the flow amount in the high temperature passage 3 increases, with the result that the jet stream of the high temperature liquid overcomes the jet stream of the low temperature liquid and the low temperature side nozzle 8 is heated to melt the oxide deposited in the periphery of the nozzle 8. While the above deposition and melting of the oxide are repeated, the deposition and melting become balanced with each other and the flow ratio α approximates the constant value. From the reading of a thermocouple 13 disposed on the low temperature side nozzle 8, the saturation temperature of the oxide in liquid metal is determined. In determining the flow ratio α, the temperature Te of liquid metal in the low temperature passage 4, the temperature Th of liquid metal in the high temperature passage 3 and the temperature Tt of liquid metal in the coupling tube 6 are measured by thermocouples 10, 11 and 12 inserted into these passages, respectively. In this case, each temperature is detected as the thermoelectromotive force of the corresponding thermocouple, and the flow ratio $$\alpha = \left( \frac{Th - Tt}{Th - Te} \right)$$

is determined by putting the so obtained data into a subtractor and a divider and may be indicated on an indication device such as a recorder or the like. As is apparent from the foregoing description, in this embodiment the saturation temperature of the oxide can be determined only by measuring the temperatures.

Figure 2:
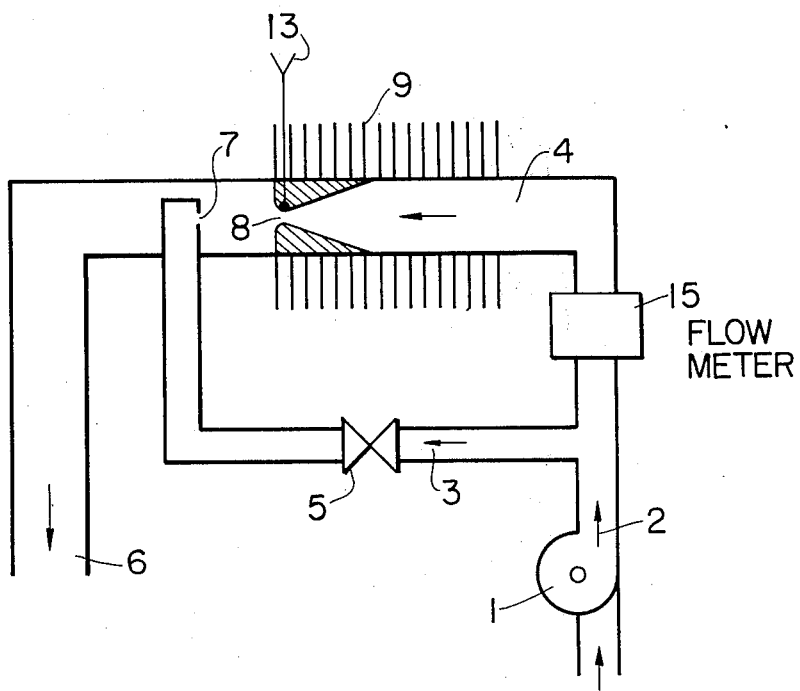
FIG. 2 is a diagram illustrating the section of another embodiment of the apparatus of this invention.

FIG. 2 illustrates the section of another embodiment of this invention. This embodiment is characterized in that although facing fluids of liquid metal are employed as in the embodiment shown in FIG. 1, the flow variation in the low temperature passage is directly measured by a flow meter 15 while in the embodiment shown in FIG. 1 the flow variation in the low temperature passage is detected by measuring the temperatures. In the embodiment shown in FIG. 2, since the flow variation in the low temperature passage caused by variation of the load or driving power of the pump 1 can be read from the flow meter 15, the measurement precision can be further improved by providing a flow meter on either the high temperature passage 3 or the main passage 2 and detecting the flow variation in the low temperature passage 4 as the variation of the flow ratio.

Figure 3:
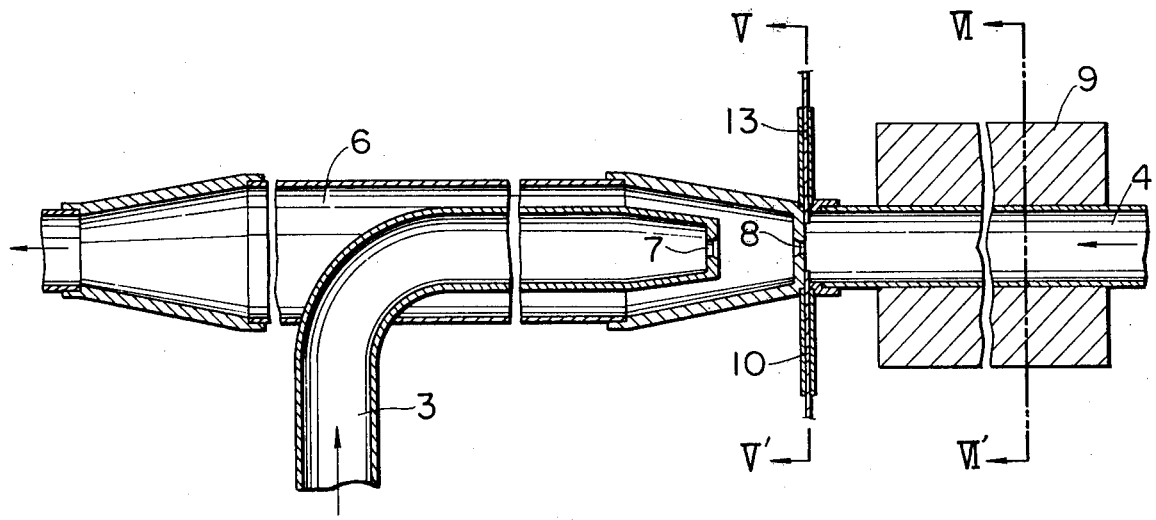
FIG. 3 is a sectional view showing detailedly and specifically an embodiment of the apparatus of this invention.

An embodiment of the apparatus of this invention is specifically illustrated in FIG. 3. In this embodiment, sodium (Na, melting point = 98° C.) is used as the liquid metal but the liquid metal is not limited to sodium alone in this invention. For instance, lithium (Li) or the like can be employed. Each of the low temperature passage 4, the high temperature passage 3 and the coupling tube 6 is composed of stainless steel and has a diameter of about 27.2mm. However, the coupling tube 6 has an increased diameter of 48.6 mm at the zone where high temperature liquid metal and low temperature liquid metal are mixed. Of course, the passage-constituting material and the passage diameter are not limited to those specified above, but they can be optionally chosen.

Figure 4:
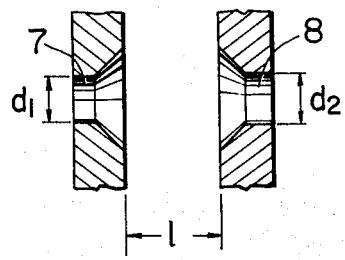
FIG. 4 is an enlarged view showing the liquid metal-projecting outlet portions of the apparatus shown in FIG. 3.

In this embodiment, orifices are used as the members 7 and 8, but as pointed above, any of orifices and nozzles can be used as the members 7 and 8. Instances of orifices 7 and 8 are shown in FIG. 4, where each orifice has a diameter of 4 mm and the distance 1 between the two orifices is adjusted to 25 mm. The orifice diameter and distance are not limited to these specific values. Any of the orifice diameter or orifice distance can be adopted as far as liquid metal injected from the orifice 7 reaches at least the orifice 8. However, it is generally preferred that the distance 1 is 6 to 7 times as long as the diameter $d_1$ of the orifice 7, though this numerical limitation is not particularly critical but any other distance can be adopted conveniently as the distance 1 in this invention. In order to increase the measurement precision, it is desired to reduce the degree of supercooling of liquid metal. For attaining this feature, it is necessary to increase the Reynold's number, and therefore, it is preferred that the diameter $d_2$ of the orifice 8 is made smaller.

Figure 5:
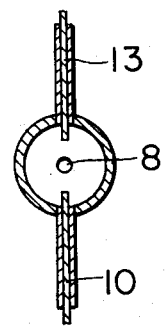
FIG. 5 is a view showing the section taken along the line V—V' in FIG. 3.

The thermocouple 13 disposed on the low temperature side orifice 8 may also act as the thermocouple 10 for the low temperature passage, as shown in FIG. 5. In the embodiment shown in FIG. 1, each thermocouple can be disposed at an optional position as far as the flow of liquid metal is not disturbed by the thermocouple and it is disposed at a zone of the branch passage where the uniform temperature is attained.

Figure 6:
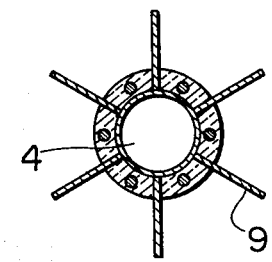
FIG. 6 is a view showing the section taken along the line VI—VI' in FIG. 3.

FIG. 6 illustrates an instance of the cooler. In this embodiment, a fin 9 of a relatively simple structure is disposed as the cooler. This heat discharge fin 9 can be cooled by appropriate cooling means (for instance, flowing a cooling medium through the fin). Of course, other cooling means may optionally be adopted.

As is apparent from the foregoing description, according to this invention it is possible to measure the saturation temperature of an oxide in liquid metal by using an apparatus of a relatively simple structure, and further, the measurement of the oxide saturation temperature can be freely controlled and adjusted and the flow conditions can be freely restored after the measurement.

It will be further recognized from the foregoing description that the oxides, the saturation temperature of which are measured, include the ordinary oxides such as $Na_2O$. Moreover the saturated temperature obtained is for use as a control of enrichment or purity of the liquid metal in a process using the liquid metal e.g. a plugging system in a fast breeder reactor. Also the reading obtained from thermocouple 13, as heretofore noted, provides an indication of the saturated temperature of the oxide in the above-described embodiments.

While the novel embodiments of the invention have been described, it will be understood that various omissions, modifications and changes in these embodiments may be made by one skilled in the art without departing from the spirit and scope of the invention.

What is claimed is:

1. An apparatus for measuring the saturation temperature of an oxide in liquid metal which comprises a main passage for liquid metal which is branched into a high temperature passage and a low temperature passage, a coupling passage for connecting said high temperature passage and low temperature passage, a liquid metal-projecting outlet disposed in said high temperature passage and opened to said coupling passage, another liquid metal-projecting outlet disposed in said low temperature passage and opened to said coupling passage in the state facing said outlet disposed in the high temperature passage, cooling means connected to in the low temperature passage between the division point from the high temperature passage and said outlet of the low temperature passage to cool liquid metal running through the low temperature passage, and temperature-detecting means disposed in the vicinity of the outlet of the low temperature passage to detect the temperature around said outlet of the low temperature passage; liquid metal projected from the outlet of the low temperature passage and liquid metal projected from the outlet of the high temperature passage, between which there is a temperature difference, being mixed with each other in the coupling passage, wherein the saturation temperature of an oxide in liquid metal is determined based on temperatures measured by said detecting means.

2. An apparatus for measuring the saturation temperature of an oxide in liquid metal according to claim 1, wherein a valve is disposed in the high temperature passage between the division point from the main passage and said outlet of the high temperature passage to adjust the flow amount of liquid metal running through the high temperature passage.

3. An apparatus for measuring the saturation temperature of an oxide in liquid metal according to claim 1, wherein a thermocouple is disposed in each of the low temperature passage, the high temperature passage and the coupling passage to detect the temperature of liquid metal in each of said passages.

4. An apparatus for measuring the saturation temperature of an oxide in liquid metal according to claim 3, wherein a means for determining the ratio of the flow amount of liquid metal running through the low temperature passage to the total flow amount of liquid metal running through the main passage based on measurement data obtained by said thermocouples and a means for measuring the saturation temperature of an oxide in liquid metal from the temperature at which the flow variation occurs, based on the flow ratio data determined by said flow ratio-determining means are further disposed.

5. An apparatus for measuring the saturation temperature of an oxide in liquid metal according to claim 1, wherein a flow meter is disposed in at least one of the low temperature passage and the high temperature passage to determine the flow variation in the low temperature passage and a means for measuring the saturation temperature of an oxide in liquid metal is disposed to measure the saturation temperature from the temperature at which the flow variation occurs, which is detected by said flow meter.

6. An apparatus for measuring the saturation temperature of an oxide in liquid metal according to claim 1, wherein said temperature-detecting means is a thermocouple.

7. An apparatus for measuring the saturation temperature of an oxide in liquid metal according to claim 1, wherein each of projecting outlet of the low temperature passage and the high temperature passage is an orifice.

8. An apparatus for measuring the saturation temperature of an oxide in a liquid metal comprising a main passage, a low temperature passage connected to said main passage and defining a low temperature metal-projecting outlet, a high temperature passage connected to said main passage and defining a high temperature metal-projecting outlet positioned so that liquid metal ejected therefrom reaches said low temperature metal-projecting outlet, a coupling passage connecting said high temperature metal-projecting outlet and said low temperature metal-projecting outlet, cooling means connected to said low temperature passage, and temperature detecting means disposed in the vicinity of said low temperature metal-projecting outlet for detecting the temperature around said low temperature metal-projecting outlet.

9. An apparatus for measuring the saturation temperature of an oxide in liquid metal according to claim 8, further comprising pump means in said main passage for pumping liquid metal therethrough.

* * * * *